US008822956B2

(12) United States Patent
Kalkbrenner et al.

(10) Patent No.: US 8,822,956 B2
(45) Date of Patent: Sep. 2, 2014

(54) HIGH-RESOLUTION FLUORESCENCE MICROSCOPY

(71) Applicant: Carl Zeiss Microscopy GmbH, Jena (DE)

(72) Inventors: Thomas Kalkbrenner, Jena (DE); Ingo Kleppe, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 0 days.

(21) Appl. No.: 13/852,873

(22) Filed: Mar. 28, 2013

(65) Prior Publication Data
US 2013/0256563 A1 Oct. 3, 2013

(30) Foreign Application Priority Data

Mar. 28, 2012 (DE) .......................... 10 2012 205 032

(51) Int. Cl.
*G01N 21/64* (2006.01)
(52) U.S. Cl.
CPC ............ *G01N 21/64* (2013.01); *G01N 21/6428* (2013.01); *G01N 21/6458* (2013.01)
USPC ...................................................... 250/459.1
(58) Field of Classification Search
USPC .......................................... 250/458.1, 459.1
See application file for complete search history.

(56) References Cited

U.S. PATENT DOCUMENTS

| 2008/0182336 A1 | 7/2008 | Zhuang et al. |
| 2010/0303386 A1 | 12/2010 | Enderlein |
| 2012/0092479 A1 | 4/2012 | Folling |

FOREIGN PATENT DOCUMENTS

| WO | WO2009/106602 A1 | 9/2009 |
| WO | WO2011/135049 A1 | 11/2011 |
| WO | WO2012/000923 A1 | 1/2012 |

OTHER PUBLICATIONS

Thomas Dertinger, et al., "Achieving increased resolution and more pixels with Superresolution Optical Fluctuation Imaging (SOFI)", ©*2010 Optical Society of America*, 11 Pgs.
Stefan Geissbuehler, et al., "Comparison between SOFI and STORM", ©*2011 Optical Society of America*, 13 Pgs.
Cristiano Niclass, et al., "A 128x128 Single-Photon Image Sensor With Column-Level 10-Bit Time-to-Digital Converter Array", *IEEE Journal of Solid-State Circuits*, vol. 43, No. 12, Dec. 2008, 13 Pgs.
Jerker Widengren, "Fluorescence-based transient state monitoring for biomolecular spectroscopy and imaging", *J.R. Soc. Interface* (2010) 7, 11 Pgs.
Dertinger e al., "Fast, background-free, 3D super-resolution optical fluctuation imaging (SOFI)", PNAS Early Edition, Dec. 14, 2009, 6 pages.
Heilemann et al., "Super-resolution imaging with small organic fluorophores", Microscopy, Aug. 7, 2009, 12 pages.

*Primary Examiner* — Mark R Gaworecki
(74) *Attorney, Agent, or Firm* — Patterson Thuente Pedersen, P.A.

(57) ABSTRACT

A microscopy method for producing a high-resolution image of a 2-dimensional sample. The method includes exciting statistically blinking fluorophores in a sample by irradiating the sample with illumination radiation, repeatedly imaging the sample onto a spatially resolving detector in an image field that covers only a part of the sample to thereby obtain a frame sequence, generating an image from the frame sequence, the image having a spatial resolution increased beyond the optical resolution limit using a cumulant function, moving the position of the image field on the sample at least once and repeating the imaging and generating steps to obtain one image for each position of the image field, and combining the resultantly obtained images to form a complete image of the sample.

14 Claims, 4 Drawing Sheets

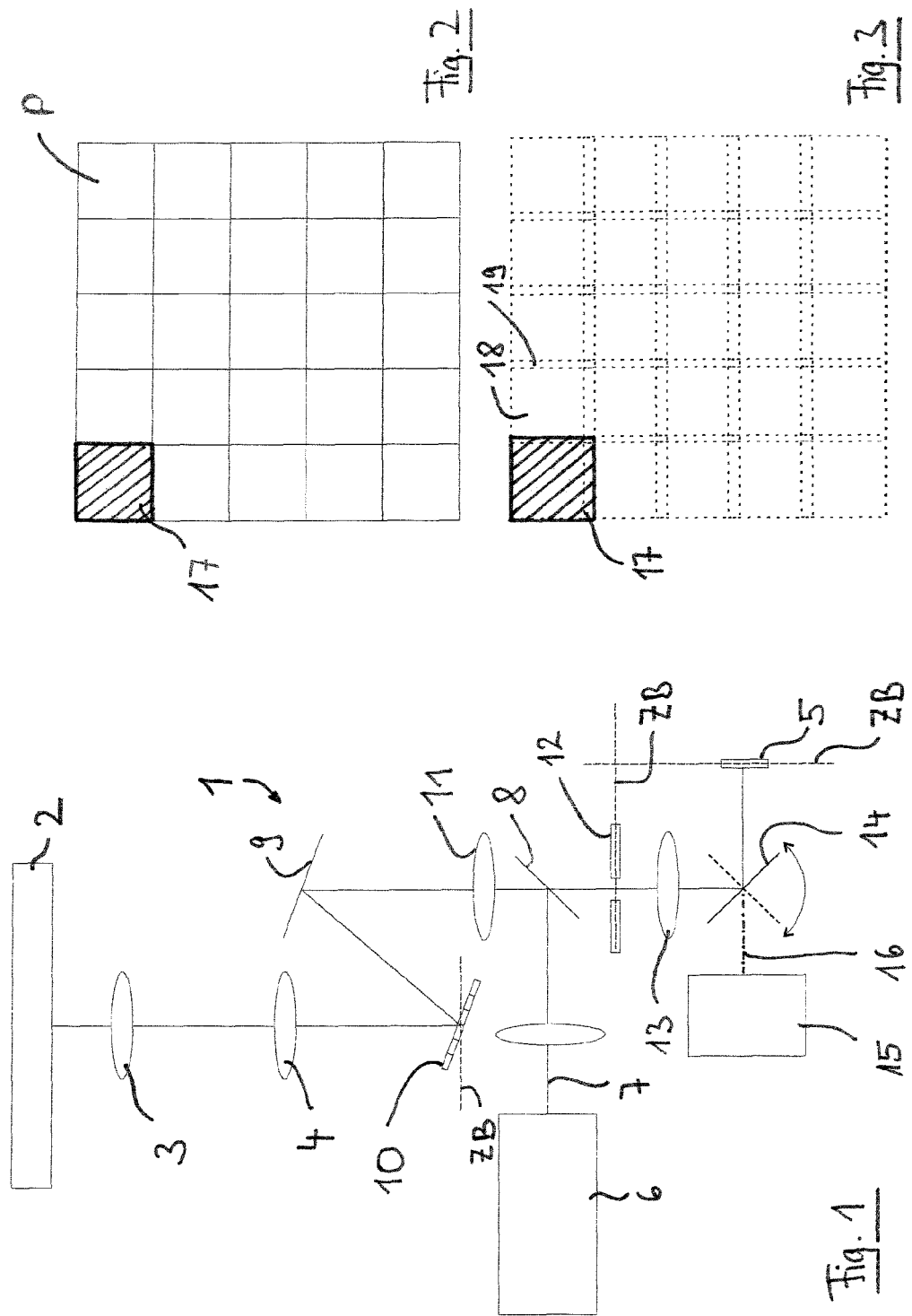

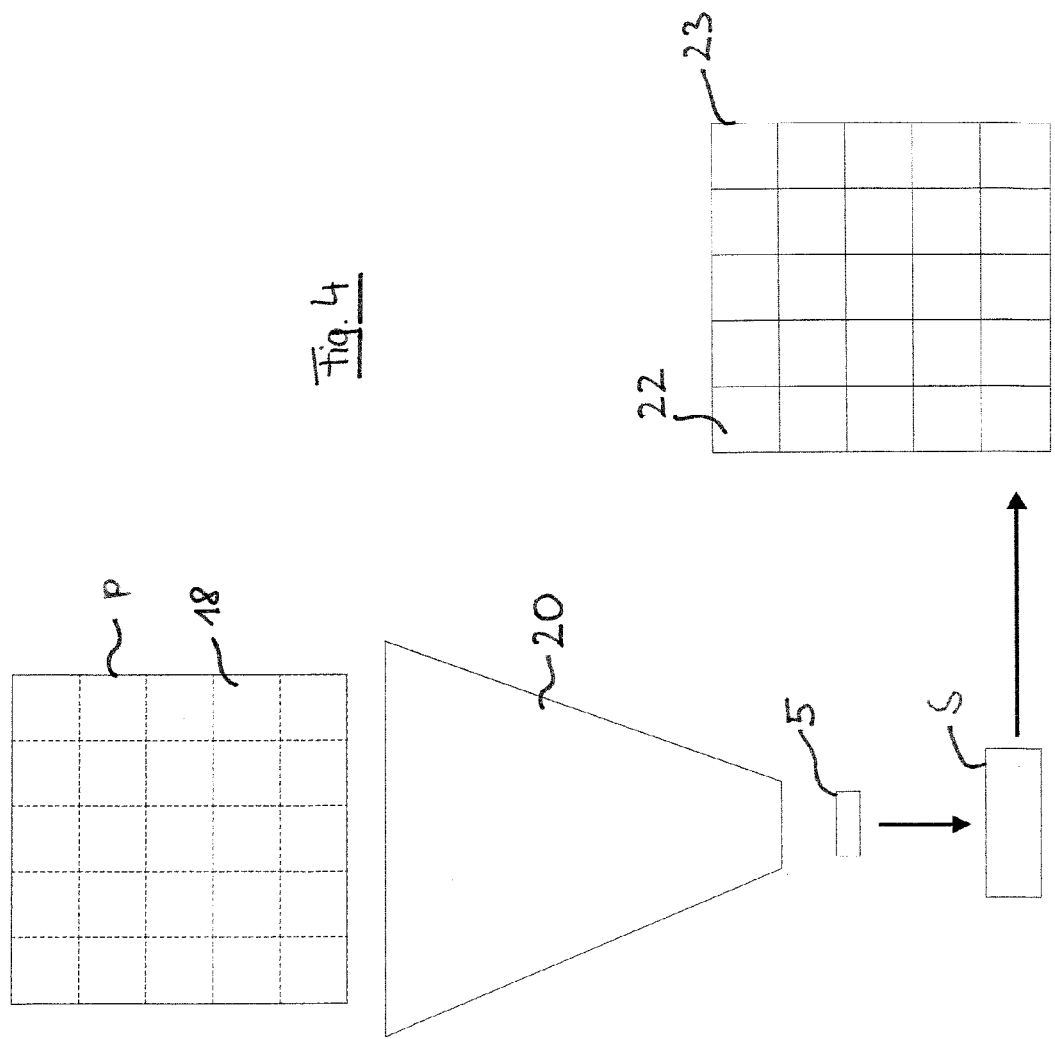

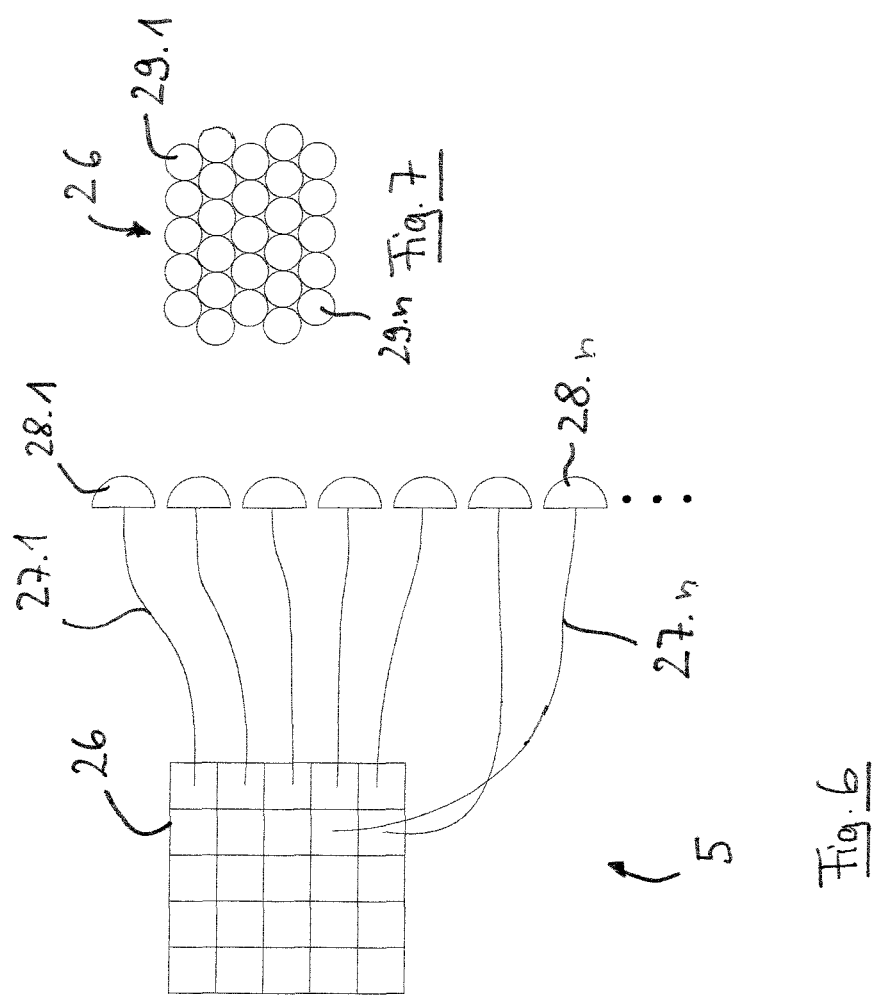

HIGH-RESOLUTION FLUORESCENCE MICROSCOPY

RELATED APPLICATIONS

This application claims the benefit of German Patent Application DE 102012205032.9, entitled HIGH RESOLUTION FLUORESCENCE MICROSCOPY, and filed on Mar. 28, 2012, said application being hereby fully incorporated herein by reference.

FIELD OF THE INVENTION

The invention relates to a microscopy method and a microscope for producing a high-resolution image of a fluorescing sample.

BACKGROUND OF THE INVENTION

The examination of samples by means of microscopy is a broad technical field for which there are varied technical solutions. Starting from the standard light microscopy, widely different microscopy methods have evolved.

A standard field of use of light microscopy for examining biological preparations is fluorescence microscopy. In this process, particular dyes (so-called fluorophores) are used for the specific tagging of samples (e.g. of cell structures). The sample is illuminated by excitation radiation and the fluorescence radiation excited is recorded by suitable detectors. A dichroic beam splitter is usually provided in the light microscope in combination with block filters which split the fluorescence radiation from the excitation radiation and enable the fluorescence to be observed alone. Through this procedure, the light microscope can reveal individual, differently colored cell structures. Of course, different structures of a sample can also be simultaneously colored with different dyes attaching specifically to different structures of the sample. This procedure is called multiple luminescence. Samples which luminesce per se, and thus without added tagging substance, can also be surveyed.

Different approaches have recently been developed to obtain a resolution beyond the diffraction limit that follows from laws of physics. These microscopy methods are characterized in that they provide the user with a higher lateral optical resolution compared with a standard microscope. In this description, such microscopy methods are called high-resolution microscopy methods, as they achieve a resolution beyond the optical diffraction limit. Diffraction-limited microscopes, on the other hand, are called standard microscopes.

High-resolution widefield microscopy methods are disclosed in: T. Dertinger et al., "Fast, Background-Free, 3D Super-Resolution Optical Fluctuation Imaging (SOFI)", PNAS (2009), pp. 22287-22292; "Achieving Increased Resolution and More Pixels with Superresolution Optical Fluctuation Imaging (SOFT)", Opt. Express, 30.08.2010, 18(18): 18875-85, doi: 10.1364/IE.18.018875; and S. Geissbuehler et al., "Comparison Between SOFI and STORM", Biomed. Opt. Express 2, 408-420 (2011). All of the foregoing references are hereby fully incorporated herein by reference. These methods use blinking characteristics of a fluorophore. If the fluorophores of a sample blink statistically and independently of one another, an imaging of the sample by suitable filtering with a so-called cumulant function achieves a significant increase in resolution beyond the physically specified optical resolution limit. An example of such a cumulant function is the second-order autocorrelation function. To produce a high-resolution image, a sample is excited and imaged in widefield. A sequence of frames is recorded and then combined using the cumulant function into one image which then has a higher resolution. This method is known in the art as the "SOFI" method, an abbreviation of the term "Super-Resolution Optical Fluctuation Imaging."

In the SOFI method, a frame sequence with as many different blinking states as possible of all the fluorophores added to the sample or intrinsically present in the sample is required. At the same time, the camera used must be capable of recording this blinking over time and simultaneously offering a high spatial resolution. In the realization of the SOFI principle, as few fluorophores as possible should change their fluorescent state in a frame. The frame acquisition frequency must therefore be much higher than the blinking frequency of the fluorophores. In practice, due to the time response of available cameras, the range of possible fluorophores is therefore severely limited; only fluorophores for which the blinking rate is slow enough for the cameras employed, can be used. In the publication of Dertinger et al. cited above, so-called quantum dots are used which display a statistical blinking at almost all time scales. The vast majority of the fluorophores that have been developed in the state of the art for the most varied sample substances cannot be used in the SOFI method.

SUMMARY OF THE INVENTION

An object of embodiments of the invention is to provide a high-resolution microscopy method according to the SOFI principle with which the limitations described above are overcome and a wider range of the fluorophores or samples can be used.

This object is achieved according to embodiments of the invention by a microscopy method for producing a high-resolution image of a 2-dimensional sample, wherein the method can include the following steps:

a) providing the sample with a marker comprising fluorophores which, upon excitation, emit statistically blinking fluorescence radiation or using a sample which comprises such fluorophores, b) exciting the fluorophores to such fluorescence by irradiating the sample with illumination radiation, c) repeatedly imaging the sample in an image field, which covers only a part of the sample, onto a spatially resolving detector, to obtain a frame sequence, d) generating from the frame sequence an image which has a spatial resolution increased beyond the optical resolution of the imaging wherein a cumulant function which evaluates in the frame sequence intensity fluctuations in the image sequence which are caused by the blinking of the fluorophores, e) moving the position of the image field on the sample at least once and repeating steps c) to d) to obtain one image per position of the image field, and f) combining the obtained images to form a complete image of the sample.

Embodiments of the invention enable the microscopy method according to the SOFI principle to be carried out with fluorophores having a blinking behavior which could not be resolved in conventional widefield cameras. Accordingly, the SOFI principle can be used with conventional fluorescent dyes by using an image field which covers only a small part of the sample to be recorded. This image field is imaged onto a camera which now can have a much better temporal resolution compared with conventional widefield cameras. By moving the image field into different positions, the full sample is still recorded with the required high spatial resolution. This movement is effected by a suitable image field moving device provided in the microscope.

The movement can also be tailored to certain sample structures. In some embodiments, it is preferred to evaluate every produced image in respect of sample structures and to make the next position of the image field dependent on the result of this evaluation. It has proved surprisingly advantageous if the frame sequence obtained for each position of the image field is converted into a high-resolution image directly according to the SOFI principle. These high-resolution images can then be combined to form a final (naturally also high-resolution) image. Compared with a combination on a frame sequence level (i.e. of the frames of the frame sequences), for the different positions of the image field, an improved statistical independence of the blinking states is obtained. It is then possible to provide an overlap area between the images which facilitates the combining to form the final image. Finally, the gradually forming images can be used to specify the position in each case for the image field of the next image.

Thus one embodiment of the microscopy method tracks structures in the sample with high resolution, and does not image the whole surface area of the sample. A further advantage is that the same range of frame sequences (i.e. the number of frames produced per frame sequence), need not be used for all positions of the image field. In an area of the sample in which there are comparatively few fluorophores, fewer frames in a frame sequence suffice to produce a high-resolution image with the SOFI principle. The approach according to embodiments of the invention, for producing a separate (high-resolution) image from a frame sequence for each image field position, thus contributes to a further acceleration of the production of a final (i.e. full) image of the sample.

The principle according to embodiments of the invention achieves a significant acceleration of the image acquisition, as rapid detectors can be used, having a number of pixels which would not be sufficient for imaging with the SOFI principle in normal widefield. If, for example, an SPDA array with 128×128 pixels is used, as is known from Niclass et al., IEEE Journal of Solid State Circuits 43, page 2977, 2008, a total of 5×5 different image field positions is required for a typical 50-μm sample field. Due to the high working speed of the detector, the acquisition of a frame sequence with 3,000 frames then requires approximately 3 ms, with the result that the total acquisition time (by this is meant the sum of the integration times which the detector requires for the image acquisition) is 25×3 ms=75 ms. Taking into account the time required to move the image field into the respective new position, a total acquisition time of less than 100 ms is achieved in embodiments of the invention. Added to this, naturally, is also the time for processing the frame sequences into the images. This is negligible for the overall image acquisition time, as the processing can also be carried out afterwards (i.e. "offline"). In contrast, however, a high-resolution widefield camera, as previously known in the art, typically requires per frame at least an integration time of 100 ms, with the result of a total acquisition time of 5 minutes.

Thus, in addition to the fact that conventional fluorophores have a blinking frequency that would not be resolvable at all with an integration time of 100 ms per frame as with prior art systems and methods (the whole sample would then emit light in the frame), a drastic acceleration of the image acquisition compared to those prior art systems and methods is thus achieved according to embodiments of the invention.

It is not only in respect of the fluorophores that a new range of applications is opened up. Additionally, samples which change over time at a time scale (e.g. as a result of processes taking place in the sample) can also be microexamined that could not be recorded at all with state of the art acquisition lasting several minutes.

In an embodiment of the invention, the acquisition duration for one position of the image field is set to less than 1 s, preferably to less than 100 ms. Furthermore, in an embodiment the acquisition time for the full image is preferably set to less than 60 s, preferably to less than 1 s.

The position of the image field can be moved particularly easily by means of an image field moving device which has an adaptive mirror or a digital micro-mirror device (DMD) which is combined with a facet mirror. The adaptive mirror or the DMD is arranged in an intermediate image plane of the imaging of the sample. The image field is moved over the sample by suitable control of the adaptive mirror or of the DMD.

For rapid image acquisition, it can be advantageous to select the number of frames per frame sequence as a function of the number of fluorophores emitting light in one frame. In one embodiment, an average brightness value can be ascertained every frame which value expresses the ratio of bright to dark image constituents or pixels. The number of the frames (i.e. the length of a frame sequence), is then set as a function of this ratio.

The principle according to embodiments of the invention addresses essentially the imaging of the sample. In order to avoid an unnecessary exposure of the sample to illumination radiation, which can produce a so-called photobleaching or photodamage to the sample, a further development irradiates the sample only in the image field. This can be particularly easily achieved in that the illumination radiation is coupled into the microscope beam path before (when seen in illumination direction) the image position of the field moving device.

Independently, the ratio of dark time to bright time of the blinking and the blinking probability of the fluorophores can be optimized. A ratio of bright to dark fluorophores of 1:1 is optimal, as then on average in every frame half of all fluorophores will emit light. Then, the number of required frames is minimized.

It is therefore to be preferred with respect to a rapid image acquisition to set a bright/dark time ratio of the blinking fluorophores by adjusting illumination parameters (e.g. the spectral composition of the illumination radiation or the intensity of the illumination radiation), and preferably to adapt the ratio to the given frame acquisition rate of the detector. Furthermore, through said illumination parameters, a blinking parameter of the fluorophores can be adapted, which blinking parameter influences at least one of the dark time and a transition probability between dark and bright state of the blinking; both with the aim of achieving or approaching the mentioned optimum ratio of 1:1.

In addition to influence through illumination radiation, some embodiments utilize a manipulation of the sample or of the marker to chemically control a lifetime of the fluorophores in which lifetime fluorescence radiation is emitted (bright state) or no fluorescence radiation is emitted (dark state). Such embodiments can be directed at populations with a transition probability between bright and dark of 0.5, if the lifetimes of the bright and the dark state are the same.

The image field positions are preferably chosen such that there is an overlap area between adjacent image fields. This facilitates the combining of the images to form the complete image.

It will be appreciated by those of skill in the art that the features mentioned above and those yet to be explained below can be used, not only in the stated combinations, but also in other combinations or alone, without departing from the spirit and scope of the present invention.

BRIEF DESCRIPTION OF THE FIGURES

The invention is explained in further detail below by way of example with reference to the attached drawings in which:

FIG. 1 is a schematic representation of a microscope for carrying out a high-resolution microscopy method;

FIG. 2 is a top view of a surface of a sample with different positions of an image field of the microscope of FIG. 1;

FIG. 3 is a representation similar to FIG. 2 to illustrate an overlap between adjacent image fields;

FIG. 4 is a schematic representation relating to the recording of a larger sample with the microscope of FIG. 1;

FIGS. 6 and 7 are schematic representations of a detector embodiment of the microscope of FIG. 1 or FIG. 5.

Figure 5:
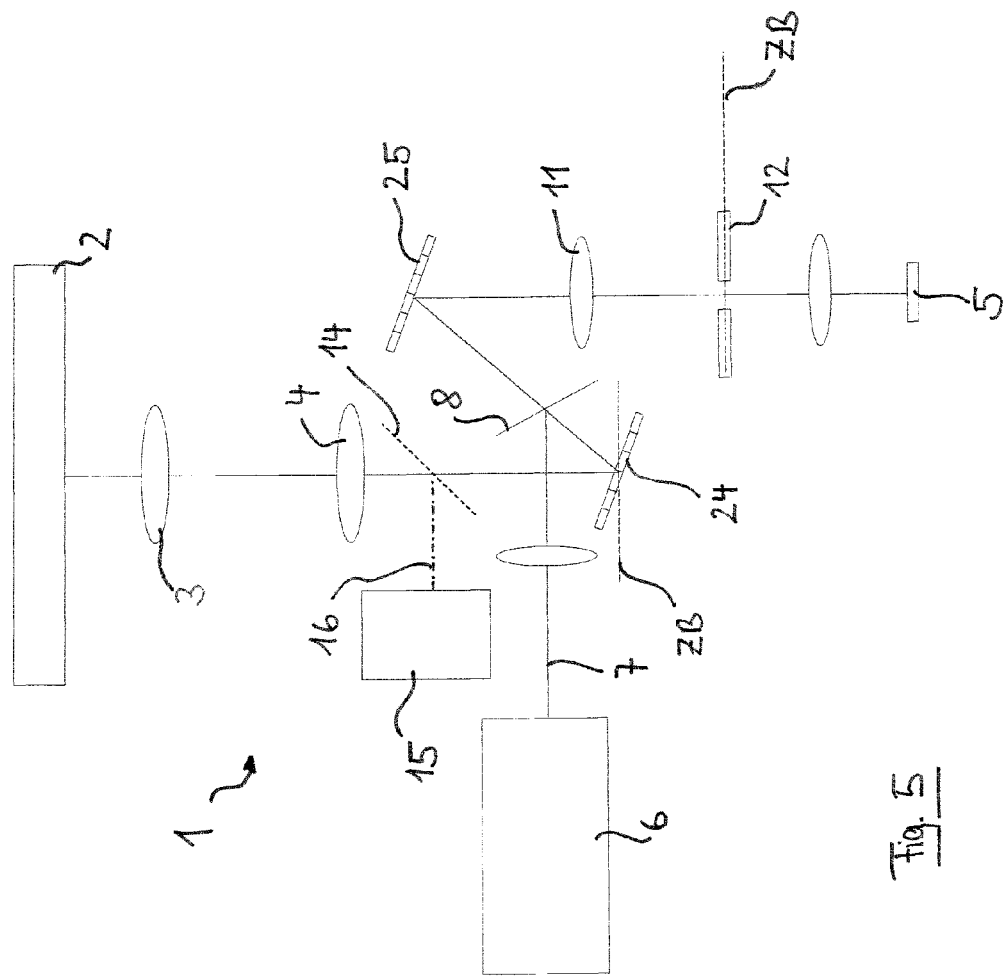
FIG. 5 is a microscope similar to that of FIG. 1, which differs in respect of a deflection unit for moving the image field position.

While the present invention is amenable to various modifications and alternative forms, specifics thereof have been shown by way of example in the drawings and will be described in detail. It should be understood, however, that the intention is not to limit the present invention to the particular embodiments described. On the contrary, the intention is to cover all modifications, equivalents, and alternatives falling within the spirit and scope of the present invention.

DETAILED DESCRIPTION

FIG. 1 depicted schematically a microscope to carry out a method for high-resolution microscopy according to the SOFI principle. The microscope 1 images a sample 2 having a 2-dimensional structure. A sample surface of the sample 2 is imaged. The microscope 1 has an imaging beam path comprising an objective 3 as well as a further lens 4, which image the sample surface. A part of the sample surface is imaged onto a detector 5, wherein an image field which is smaller than the sample surface is imaged onto the detector 5.

The sample 2 is exposed to illumination radiation 7 by a laser 6 which is one possible example of an illumination means wherein the illumination radiation 7 is guided by an illumination beam path. The illumination radiation 7 excites the emission of fluorescence radiation in the sample. The illumination beam path is coupled to the imaging beam path via a lens system (not depicted) and a beam splitter 8. After the beam splitter 8, the illumination and imaging beam paths are combined and guided via a deflection mirror 9 and an adaptive mirror 10. The deflection mirror 9 keeps the beam path compact. The adaptive mirror 10 has mirror segments which can be controlled individually. It is arranged in an intermediate image plane ZB of the combined imaging and illumination beam path. The adaptive mirror 10 is one possible example of an image field moving device for moving the image field, which is imaged onto the detector 5, over the sample surface, as will be explained further below.

A diaphragm 12 which is likewise arranged in an intermediate image plane assists in the image field selection. A lens 13 and a movable mirror 14 in the imaging beam path guide the image of the sample 2 to the detector 5 which lies in an image plane ZB.

The movable mirror 14 may have two positions. In a second position, the mirror 14 reflects the radiation to a customary widefield camera 15. Then, the sample can be observed with the widefield camera 15. In a first position of the mirror 14, the radiation is reflected to the detector 5. Movable mirror 14 and camera 15 are optional. When the mirror 14 is in the second position and the camera 15 operates, the diaphragm 12 can be set to wide, or taken out of the beam path, with the result that the whole sample field of the sample 2 is illuminated to the camera 15.

The imaging beam path further includes a lens 11 which, like the lens 13, effects an intermediate imaging. The lens 11 generates the intermediate image plane ZB in which the diaphragm 12 lies, and the lens 13 generates the intermediate image plane ZB in which the detector 5 is arranged.

The function of the image field moving device, realized in the embodiment of FIG. 4 by the adaptive mirror 10, can be seen from FIG. 2 which shows a top view of a sample field P to be imaged at the sample 2. Reference numeral 17 denotes the image field which is much smaller than the sample field P. The image field 17 is shifted by the adaptive mirror 10 over the sample field P. The corresponding shift positions and resultant positions of the image field 17 are shown schematically in FIG. 2.

With reference to FIG. 3, the adaptive mirror 10 brings the image field 17 into different positions 18 located such that there is an overlap area 19 between adjacent positions 18. This is optional, but facilitates the subsequent combining of individual images to form a complete image which covers the full sample field P.

In embodiments including the adaptive mirror 10, the mirror 10 may include one or more grouped elements which move the image field 17 over the sample field P. The size of the image field 17 which is imaged onto the detector 5 can be specified by the surface area of the detector itself and by the size of the diaphragm 12. Diaphragm 12 improves the imaging, but is not mandatory. If it is omitted, the corresponding intermediate image plane ZB and the optical means for producing it can be dispensed with, too.

Detector 5 is a detector array having a number of pixels which, if the total sample field P were to be imaged, would not reach the optical resolution limit which is ultimately limited by the objective 3. The size of the image field 17 and the magnification ratio of the microscope 1 can be chosen such that a resolution limited length in the sample corresponds to the size of a pixel on the detector. By moving the image field 17, a detector which has a small number of pixels and a high measuring speed can be used. In contrast, with electronic detectors as customarily used in the art, the measuring speed is limited by the integration time and the readout time of the detector. The detector 5 of the microscope 1, however, is for example an avalanche photodiode, a photomultiplier, or a GaAsP hybrid detector, which are all much quicker than conventional CMOS- or CCD-based area detectors.

FIG. 4 illustrates the measuring method which is carried out by the microscope 1. The sample field P is imaged by an optical system 20, which corresponds for example to the optical system of the microscope 1, onto a spatially resolving detector 5, wherein the optical imaging is carried out such that a diffraction-limited length which defines the maximum resolution, corresponds on the detector to the size of a detector pixel. The image field recorded by the optical system 20 is thus much smaller than the sample field P to be imaged in the end. In order to record the whole sample field P, the image field is brought into different positions 18, depicted schematically for the image field P in FIG. 4. For every position, the sample 2 is excited to blinking fluorescence according to the SOFI principle, and a frame sequence, the frames of which each contain different blinking states of the sample 2 is acquired by means of the detector 5 for the current position 18 of the image field.

The frame sequence is then converted to a high-resolution image in a SOFI processing S. For example the principle described by Dertinger et al., as previously incorporated herein by reference, may be used. The refinement of Dertinger's principle as disclosed in "Achieving Increased Resolution and More Pixels with Superresolution Optical Fluctuation Imaging (SOFI)", Opt. Express, 30.08.2010, 18(18): 18875-85, doi: 10.1364/OE.18.018875, may also be used, said publication also having been previously incorporated by reference, supra.

As a result of the SOFI processing, an image 22 is obtained which reproduces the sample with high resolution for the current position 18 of the image field 17. The procedure is then repeated for different positions 18, and the obtained images 22 are combined to form a complete image 23. This can cover the whole sample field P, or also only certain predefined sections (e.g. structures of interest in the sample).

FIG. 5 shows a modification of the microscope 1 (i.e. a further embodiment of the optical system 20). Elements or components which correspond in terms of structure or function to those of the microscope of FIG. 1 bear the same reference numbers in FIG. 5 and will therefore not be described again. The major difference between the microscope of FIG. 1 and the microscope of FIG. 5 is the image field moving device used in each. In the embodiment according to FIG. 5, the image field moving device comprises a DMD 24, the individual mirrors or mirror groups of which are actuated such that they bring the image field 17 into the desired position 18 on the sample field P. All segments of the adaptive mirror 10 which are not used for imaging of the image field 17 in the current position 18 are moved to a position which ensures that these mirror portions do not participate in the imaging.

The DMD 24 selects sections of the imaging beam path which are necessary for the current size or position 18 of the image field 17. A facet mirror 25, the facets of which are likewise adapted to the positions 18 of the image field 17, ensures the corresponding angle change.

The movable mirror 14 is formed in the microscope 1 of FIG. 5 such that it can selectively be moved into the beam path in order to illuminate the sample in widefield. The sample is then observed via an eyepiece, which observation is advantageous for example for adjustment purposes etc.

In the embodiments of FIG. 1 and FIG. 5, the microscope 1 advantageously couples in the illumination radiation 7 via the image field moving device. This causes the sample to be illuminated and excited only in the image field 17 in which it is also imaged. Excess photo exposure of other parts of the sample, which could lead to undesired photobleaching, is thus avoided.

For moving the image field 17, the element arranged in an intermediate image plane ZB can be replaced by a scanning device (e.g. a scanner mirror pair) which scanner lies in a pupil (e.g. like the scanner of a laser scanning microscope (LSM)). In contrast to an LSM, the scanned spot realizing the image field is however much (usually many times, e.g. 10-100 times) larger than the diffraction limit, as otherwise the imaging onto the spatially resolving detector 5 would deliver no image information. Such microscope can be based on an LSM. Such modification can be used with all embodiments.

FIG. 6 depicts an alternative embodiment of the detector 5. As depicted, detector 5 includes fiber array feeding detector elements. The end surfaces of a bundle of optical fibers 27.1 to 27.$n$ are combined in a coupling-in surface 26 which lies in an intermediate image plane ZB. Each optical fiber 27.1 to 27.$n$ couples its radiation onto a detector element 28.1 to 28.$n$. Particularly rapid individual detectors can thereby be used.

The geometric size of each detector element and also a packing density thereby achievable plays no further part, as the spatial resolution of the detector array is defined by the sizes and arrangements of the ends 29.1 to 29.$n$ of the optical fibers 27.1 to 27.$n$ at the coupling-in surface 26. This fiber-based detector design can be used in all embodiments of the detector 5.

In all embodiments, a zoom lens system can be provided between the sample 2 and DMD 24 to effect an adjustment of the image field size. Resolution and image acquisition time can thereby be optimized. In addition, but also alternatively, a zoom lens system can be provided between diaphragm 12 and detector 5. The pixel size effective for detecting the image field can thus be adjusted. Thus, an optimum of resolution and image acquisition time can be maintained. This is advantageous for the SOFI process because at higher orders, the SOFI resolution is limited by the camera pixels. The zoom lens system reaches the same resolution as the more laborious XC-SOFI method according to the above incorporated Opt. Express publication, which reduces the effective pixel size via a cross-correlation.

The blinking of the fluorophores required for the SOFT principle comes from a transition from a first, fluorescing state to a second, non-fluorescing state. A non-fluorescing state means every state which lacks the fluorescence radiation which is evaluated for the image. Such non-fluorescing state thus can be a state in which a fluorophore emits light in a different fluorescence spectral range.

The transition probabilities from the first to the second state can be modified, for example by chemical influences, temperature influences or illumination influences, as is known for example from Heilemann et al., Angewandte Chemie 121, p. 7036, 2009, hereby fully incorporated herein by reference.

The SOFI principle is particularly efficient if, at the given image acquisition rate or image integration time, the ratio between fluorophores emitting light and fluorophores not emitting light is 1:1 or at least about 1:1. If these two states have the same lifetimes, the transition probability between the first and the second state as well as between the second and the first state should ideally be 0.5. This can be achieved by corresponding manipulation of the sample by means of chemical influencing, thermal influencing or illumination influencing. One embodiment optimizes the transition probability by adjusting the irradiated spectral distribution with the aim of achieving the named optimum ratio 1:1. The SOFI principle requires transition probabilities which differ substantially from other microscopy methods. The PALM principle for example (also called dSTORM) requires conditions in which the vast majority of the fluorophores are in a dark state.

In order to ensure that preferably half of the fluorophores are in a bright state, the dark time must also be taken into consideration in addition to the transition probability. Even when the transition probability of bright to dark is 0.5, the optimum ratio of 1:1 would not be achieved if the dark states have a significantly longer lifetime. To modify the transition probability and dark time is therefore particularly preferably (and quite independently of the imaging of an image field which is smaller than a sample field) to optimize the ratio of fluorophores emitting light to fluorophores not emitting light. The optimum value 1:1 can be obtained or at least approached by suitably setting at least one of a transition probability and a dark lifetime (or bright lifetime) and adjusting them to the image acquisition rate or integration time.

The foregoing descriptions present numerous specific details that provide a thorough understanding of various embodiments of the invention. It will be apparent to one skilled in the art that various embodiments, having been disclosed herein, may be practiced without some or all of these specific details. In other instances, components as are known to those of ordinary skill in the art have not been described in detail herein in order to avoid unnecessarily obscuring the present invention. It is to be understood that even though numerous characteristics and advantages of various embodiments are set forth in the foregoing description, together with details of the structure and function of various embodiments, this disclosure is illustrative only. Other embodiments may be constructed that nevertheless employ the principles and spirit of the present invention. Accordingly, this application is intended to cover any adaptations or variations of the invention.

For purposes of interpreting the claims for the present invention, it is expressly intended that the provisions of 35 U.S.C. §112(f) are not to be invoked unless the specific terms "means for" or "step for" are recited in a claim.

What is claimed is:

1. A microscopy method for producing a high-resolution image of a sample that contains fluorophores that, upon excitation, emit statistically blinking fluorescence radiation, the method comprising:
   a) exciting the fluorophores in the sample by irradiating the sample with illumination radiation;
   b) repeatedly imaging the sample onto a spatially resolving detector in an image field that covers only a part of the sample, to obtain a frame sequence;
   c) generating an image from the frame sequence, the image having a spatial resolution increased beyond the optical resolution limit using a cumulant function;
   d) moving the position of the image field on the sample at least once and repeating steps b) and c) to obtain one image per position of the image field, and
   combining the obtained images from step d) to form a complete image of the sample.

2. The method according to claim 1, comprising using as the spatially resolving detector, a spatially resolving avalanche photodiode, a spatially resolving photomultiplier, a spatially resolving GaAsP hybrid detector, or an optical fiber bundle in which individual optical fibers of the optical fiber bundle are each connected to a detector element.

3. The method according to claim 1, wherein an acquisition time for each position of the image field is less than 1 second.

4. The method of claim 3, wherein the acquisition time for each position of the image field is less than 100 ms.

5. The method according to claim 1, wherein an acquisition time for the complete image is less than 60 seconds.

6. The method according to claim 5, wherein the acquisition time for the complete image is less than 1 second.

7. The method of claim 1, further comprising using an adaptive mirror arranged in an intermediate image plane, or a DMD combined with a facet mirror arranged in an intermediate image plane, to move the position of the image field on the sample.

8. The method of claim 1, further comprising using a biaxially deflecting mirror device arranged in a pupil to move the position of the image field on the sample.

9. The method according to claim 1, wherein the sample is irradiated with the illumination radiation only in the image field.

10. The method according to claim 1, wherein the positions of the image field are arranged such that there is an overlap image area for adjacent positions.

11. The method according claim 1, further comprising controlling a spectral composition of the illumination radiation to set a bright/dark time ratio of the blinking of the fluorophores.

12. The method according to claim 1, further comprising controlling an intensity of the illumination radiation to set a bright/dark time ratio of the blinking of the fluorophores.

13. The method of claim 1, further comprising adjusting one or more blinking parameters of the fluorophores, the blinking parameters comprising at least one of a dark time and a transition probability between dark and bright state of the fluorophores.

14. The method of claim 1, further comprising adapting a readout rate of the detector to blinking parameters of the marker or of the sample.

* * * * *